United States Patent [19]

Chirikjian

[11] 4,342,833

[45] Aug. 3, 1982

[54] IMMOBILIZED RESTRICTION ENDONUCLEASES

[75] Inventor: Jack G. Chirikjian, Rockville, Md.

[73] Assignee: Bethesda Research Laboratory, Rockville, Md.

[21] Appl. No.: 896,811

[22] Filed: Apr. 17, 1978

Related U.S. Application Data

[63] Continuation-in-part of Ser. No. 801,854, May 31, 1977, abandoned.

[51] Int. Cl.³ .................... C12N 11/10; C12N 9/22; C12P 19/34
[52] U.S. Cl. .................................. 435/178; 435/91; 435/172; 435/174; 435/176; 435/179; 435/180; 435/199
[58] Field of Search ........ 195/28 N, 63, 68, DIG. 11; 435/89, 90, 91, 172, 174, 175, 177, 178, 180, 181, 199

[56] References Cited

U.S. PATENT DOCUMENTS 3,909,358 9/1975 Stanley et al. ..................... 195/63
4,013,514 3/1977 Wildi et al. ....................... 195/63 X
4,039,382 8/1977 Thang et al. ..................... 195/28 N

OTHER PUBLICATIONS

Roberts, R. J., Restriction Endonucleases, Critical Reviews in Biochemistry, Nov. 1976 (pp. 123, 151, 152, 153 & 163).
Zaborsky, O., Immobilized Enzymes, CRC Press, Cleveland, Ohio, 1973 (pp. 2, 30–32, 128, 129 &134–138).

Primary Examiner—David M. Naff
Attorney, Agent, or Firm—Kane, Dalsimer, Kane, Sullivan and Kurucz

[57] ABSTRACT

Restriction endonucleases are immobilized by chemically bonding the restriction endonucleases to water-insoluble matrices. The immobilized restriction endonucleases have enhanced stability and can be used to obtain deoxyribonucleic acid fragments in relatively low salt media, free of protein and ready for further use without tedious and time-consuming manipulations.

2 Claims, No Drawings

IMMOBILIZED RESTRICTION ENDONUCLEASES

CROSS-REFERENCE TO RELATED APPLICATIONS

This application is a continuation-in-part of copending application Ser. No. 801,854 filed May 31, 1977 now abandoned.

BACKGROUND OF THE INVENTION

1. Field of the Invention

The invention relates to the immobilization of enzymes and more particularly relates to immobile, site-specific, restriction endonucleases and their use to recognize and cleave specific sequences of base pairs (palindromes) within the deoxyribonucleic acid duplex.

2. Brief Description of the Prior Art

It is well established that restriction endonucleases are powerful tools in studies of genetic engineering, DNA sequencing and molecular biology. These enzymes, which are obtained by relatively simple biochemical fractionation from bacterial extracts are endowed with the ability to recognize and cleave deoxyribonucleic acids at specific sequences. These sequences (palindromes) are the signals for the sites of catalysis for the particular enzyme. To date there are over ninety known restriction endonucleases.

Prior to my invention, restriction endonucleases were physically added to specific deoxyribonucleic acid samples in vitro. The resulting reaction was then stopped. In large preparations where deoxyribonucleic acid fragments have to be recovered, endonuclease had to be first removed from the reaction mixture before fractionating the deoxyribonucleic acid fragments. Although these procedures are singly not limiting, collectively taken they are a set of tedious steps, each one of which potentially results in the loss of deoxyribonucleic acid substrate (which may be difficult to replace). These problems are magnified when secondary cleavages are to be made. For example, in many cases: (a) there may be a blocking of cleavage sites by proteins from the first crude extract, or (b) inhibition of cleavage by several undetermined factors present in extracts of the first or subsequent digestions.

Using the compounds of my invention, deoxyribonucleic acid to be digested may be incubated with a specific restriction endonuclease and the digest recovered quantitatively with simultaneous removal of the endonuclease as well as other objectionable protein materials. The restriction endonucleases and deoxyribonucleic acid may be incubated together in batches or on a mini-column and the digest fragments readily removed from the restriction endonuclease by centrifugation if batchwise digestion is executed or eluted off the mini-column in low salt buffer. In this manner, deoxyribonucleic acid fragments can be obtained in relatively low salt media, free of protein and ready to be submitted to the next step in the investigator's planned study.

SUMMARY OF THE INVENTION

The invention comprises a biochemically active, immobilized restriction endonuclease derivative, which comprises; a compound of the formula:

$$[R-X]_m]_nA \quad (I)$$

wherein R represents a biochemically active, restriction endonuclease residue following reaction of said restriction endonuclease with one of X and A; X represents the residue of a multifunctional cross-linking reagent following reaction with R and A; A is the residue of a water-insoluble, matrix material following reaction with one of R and X; m is an integer of from 0 to 4; and n is an integer of from 1 to the number of functional chemical groups available on A for coupling to R and X.

The term "biochemically active" as used throughout the specification and claims means that the derivative compound will recognize and cleave palindromes in deoxyribonucleic acids and fragments thereof in the same manner as the corresponding parent restriction endonuclease.

The term "immobilized" means that the restriction endonuclease moiety of the derivative compounds of the invention is chemically bonded to the remaining moiety of the compound.

The term "restriction endonuclease" is used herein in its commonly accepted sense as meaning a site specific endodeoxyribonuclease and isoschizomers thereof. The chemical structure of these compounds has not been established and their use and reactions are carried out empirically.

The compounds of the invention are useful to recognize and cleave palindromes from deoxyribonucleic acids and fragments thereof at specific sites. The compounds are particularly useful as reagents to map genomes and to sequence deoxyribonucleic acids (hereinafter referred to for convenience as "DNA").

Matrix bound restriction endonucleases offer several practical advantages over their soluble counterparts. The insoluble enzymes can be either packed in the form of a column or rapidly pelleted from solutions by centrifugation. These procedures allow quick and complete removal of restriction endonucleases from reaction mixtures. Such recovered enzymes are reusable several times over, permitting cleavage of large amounts of DNA with relatively few units of enzyme. Quick and complete removal of enzymes also avoids the inhibition frequently observed upon subsequent digestion by a second endonuclease. In addition, no phenol extraction is required, resulting in increased recovery of digestion products and eliminating tedious and time-consuming manipulations. These procedural advantages together with enhanced stability clearly make the compounds of the invention a valuable class of reagent.

The invention is also of the method of immobilizing site-specific restriction endonucleases while retaining their biochemical activity, i.e.; their ability to recognize and cleave specific palindromes from deoxyribonucleic acids and fragments thereof.

DETAILED DESCRIPTION OF THE PREFERRED EMBODIMENTS OF THE INVENTION

Restriction endonucleases are well known compounds as is the method of their preparation; see for example Roberts, Critical Reviews in Biochemistry, November 1976, pages 123–164. Representative of restriction endonucleases which may be immobilized by the method of the invention to prepare compounds of the formula (I) above are Alu I, Ava I, Ava II, Bal I, Bam HI, Bcl I, Bgl I, Bst E II, Eco R I, Hae II, Hae III, Hinc II, Hind II, Hind III, Hinf I, Hha I, Hpa I, Hpa II, Hph I, Hin 389I, Kpn II, Pst I, Rru I, Sau 3A, Sal I, Sma I, Sst I, Sst II, Tac I, Taq I, Xba I, Xho I and the like, many of which are commercially available (Bethesda Research Laboratories Inc., 411 N. Stonestreet Avenue, Rockville, Md. 20850). Other restriction endonucleases which may be employed and their preparation are listed in Roberts, supra., at pages 127-130.

Water-insoluble matrices forming the residue A in the above-described compounds of formula (I), are also generally well known compounds. They bear functional chemical groups capable of coupling or bonding with functional chemical groups in the moieties X of formula (I) and/or the above-described restriction endonucleases. The bond or bonds formed do not adversely affect the biochemical activity of the restriction endonuclease moiety. The matrices may be organic or inorganic in nature. Representative of inorganic matrices which may form the residue A of formula (I) are ceramics, glass, quartz, polysulfones and the like. Representative of organic matrices are water-insoluble polymers such as polyacrylamides, polyaminostyrene, polysaccharides or derivatives thereof containing hydroxyl groups and the like. Examples of water-insoluble polysaccharides or derivatives thereof containing hydroxyl groups are natural vegetable fibers such as cotton, linen, jute or Manila hemp; cellulose fibers such as regenerated fibers (e.g., viscose rayon); cellulose derivatives such as carboxymethyl cellulose, phosphocellulose, sulfomethyl cellulose, sulfoethyl cellulose, para-aminobenzyl cellulose, aminoethyl cellulose, diethylaminoethyl cellulose, triethylaminoethyl cellulose; crosslinked gels of dextran-epichlorohydrin (hereinafter referred to for convenience as "dextran gel"); dextran gel derivatives such as carboxymethyl dextran gel, diethylaminoethyl dextran gel or sulfoethyl dextran gel, other polysaccharides such as chitin, agar, agarose (the neutral galactose polymer occurring in agar) and the like.

Further representative of organic polymers are water-insoluble derivatives of the above polysaccharides such as, for example, cotton, methylcellulose, carboxymethyl cellulose, regenerated cellulose and the like which have been oxidized so that some of the glucoside units are converted to dialdehyde groups, i.e.; groups of the formula:

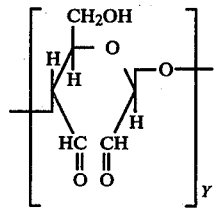 (II)

wherein Y represents an integer of from about 1000 to about 100,000. The dialdehyde groups will readily form covalent bonds with an amino group on the restriction endonuclease without inactivating the biochemical activity of the endonuclease.

The method of the invention, that is immobilizing restriction endonucleases, is preferably carried out by reacting them with a compound of the formula:

 (III)

wherein X, A and n are as previously defined, i.e.; a compound which comprises a water-insoluble matrix material as described above wherein a cross-linking agent is interposed to effect bonding to the restriction endonuclease. The cross-linking agent, represented by X in the formulae (I) and (III) above may be any of the multi-functional cross-linking agents commonly employed to bind enzymes to the above described matrix residues A. Such cross-linking agents may be tri and tetra-functional but preferably are bifunctional. The selection of a given cross-linking agent will depend of course upon the nature of the water-insoluble matrix reagent used in preparing the compounds of formula (I). Those skilled in the art will appreciate the most favorable cross-linking agents which may be employed. For example when porous glass is employed as a matrix material, 4,4'-bi(2-methoxybenzenediazonium chloride) may be used to couple together the restriction endonuclease and the glass carrier. The technique of affixing the cross-linking agent to the glass is known; see for example U.S. Pat. No. 3,930,951.

Similarly, the use of cross-linking agents or so-called "activators" to enhance the bonding capacity of polysaccharides as enzyme carrier matrices is well known. For example the polysaccharide compounds described above may be activated by reaction with an epoxy compound such as 1,4-bis-(2,3-epoxypropoxy) butane. The most widely followed technique for activating water-insoluble polysaccharides is probably by reaction with a cyanogen halide; see U.S. Pat. No. 3,914,183.

In essence then, water-insoluble matrices, both organic and inorganic in nature are used in the method of the invention to immobilize restriction endonucleases. The matrix is selected so that it contains or can be provided with suitable reactive groups such as amino groups, hydroxyl groups and carboxylic groups, to readily make possible the binding of the restriction endonuclease to the polymer with covalent linkages. Particularly advantageous is the choice of polymer particles consisting of a three dimensional network, held together by covalent linkages. Such particles even though they are swellable in water, are completely insoluble therein and are thus unable to release any of the matrix material or of the substance bound thereto by covalent linkages, e.g. during washing procedures. Examples of such polymer particles are grains of copolymers obtained by cross-linking substances containing a plurality of hydroxyl groups, such as carbohydrates and sugar alcohols, such as dextran, starch, dextrins and other polysaccharides described above and polyvinyl alcohol with a bi-functional substance, e.g. bi-functional cross-linking agents of the formula:

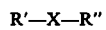 (IV)

wherein X is as before defined and R' and R" are each selected from the group consisting of halogen and epoxy groups. The term "halogen" as used herein embraces chlorine, bromine and iodine. Preferably X is the residue of an aliphatic hydrocarbon having 2 to 10 carbon atoms, inclusive, such as butane, hexane, decane and the like.

The restriction endonucleases may be bound to the monovalent moiety

 (V)

under mild conditions so that biochemical reactivity of the enzyme does not decrease. The covalent binding of the enzyme to the water-insoluble reagent cannot loosen and allow the enzyme to be washed away. The polymer matrix, cross-linked or activated may be advantageously reacted with the restriction endonuclease in an inert polar solvent such as water, at pH values of between 4 and 14. Advantageously the reaction is carried out in a buffered aqueous solution, using any inert buffer suitable for maintaining a pH within the desired range. For example, a pH of 4 to 5 can be buffered with 0.005-0.5 M, preferably 0.05 M acetate buffer, while a pH range of 5 to 8 can be maintained with a phosphate buffer of the same concentration. In the pH range of 7 to 9, suitable buffers are triethanolamine, TRIS, e.g. tris (hydroxymethylaminomethane) or boric acid/borax buffers of the same concentration and in the pH range of 9 to 11, or a carbonate/bicarbonate buffer. Also other buffers effective in the indicated pH ranges can be utilized, as the nature of the buffer is not critical so long as it is inert and within the pH range desired. Many such buffer systems can be found in the literature. The binding temperatures are of course below deactivation temperatures of the particular enzymes employed, preferably at about 0° to 37° C. The term "inert" as used herein means the buffer will not enter into or otherwise adversely affect the desired course of the reaction.

The quantitative ratio of activated polysaccharide carrier matrix to restriction endonuclease is preferably about 5:1 to 1:5, most preferably about 2:1. For purposes of the reaction, the restriction endonuclease may be provided in the buffered aqueous solution and the carrier matrix can be stirred into this solution. It is also possible to stir the endonuclease to be affixed, preferably in an aqueous buffered solution, into a carrier suspension. The reaction mixture furthermore may contain conventional stabilizers, e.g. suitable protein stabilizers such as cysteine or mercaptoethanol, and/or $Mg^{++}$ ions. Subsequently, the reaction mixture is maintained for a reaction time of from about 5 minutes to about 48 hours, normally about 1 hour, at a pH of between 4 and 14. Optional coupling pH's for a given system are readily determined by simple experimentation. Thereafter, the reaction product is isolated from the suspension in a conventional manner. Normally, the insoluble product is filtered off and washed in the usual way in order to remove the absorbed but uncoupled remainder of the restriction endonuclease. Washing is preferably with a buffer or salt solution, with a molarity of up to about 3 and a pH value of between 4 and 14, as appropriate for the particular enzyme. Suitable salts are particularly readily soluble and strongly dissociating alkali metal salts, e.g., NaCl or $Na_2SO_4$. However, it is also possible to utilize buffer solutions, optionally in a mixture with these alkali metal salt solutions.

Because of their many advantageous properties, restriction endonucleases immobilized in accordance with this invention can be utilized in a wide variety of ways. For example, they may be used in reactions as column packings, since they have good mechanical properties and high transit speeds can be obtained. More specifically, the compounds of formula (I), supra, may be packed in the form of a jacketed column and a solution of a deoxyribonucleic acid passed over and held on the column at incubating temperature (circa 37° C.). After a period of 1 to 16 hours, the enzyme bound to the carrier matrix [compound (I)] will have digested the DNA (assuming the correct palindromes were present). The fragmented DNA may then be allowed to pass off the column for further study, etc. The DNA fragments leave the column free of enzyme impurities. The column can be used repetitively for long periods of time, e.g., for at least a month when stored at room temperature between uses.

Alternatively, the compounds (I) of the invention may be simply admixed with solutions of DNA at incubating temperatures for periods of from 1 to 24 hours and thereafter separated from the digested DNA by simple filtration.

The following examples and preparations describe the manner and process of making and using the invention and set forth the best mode contemplated by the inventor of carrying out the invention, but are not to be construed as limiting. All parts are by weight unless otherwise specified.

PREPARATION 1

Oxidation of Cotton With Periodic Acid

Cotton roving (80 grams) cut in one inch long pieces is washed in a 0.1% dodecylphenol-10 mole ethylene oxide adduct, plus 0.1% sodium carbonate solution (2000 ml) for about 5 to 10 minutes by manual stirring. The resulting slurry is then filtered over a Buchner funnel and the cotton fibers recovered.

The recovered cotton fibers are then rinsed five times with 4000-milliliter aliquots of distilled water with intermittent stirring and filtering after each rinse, followed by rinsing three times with 2000-milliliter aliquots of acetone to remove the water, again with intermittent stirring and filtering after each rinse. Ultimately the washed and rinsed cotton is air dried under a hood.

The dried cotton (50 grams) is placed in a 4 liter Erlenmeyer flask and aqueous, about 0.11 M, periodic acid solution (2.5 liters; pH 1.4) added thereto. The flask is then stoppered using a polyethylene-coated stopper which resists oxidation and the outside of the flask is covered with aluminum foil so as to exclude light. Thereafter, the flask is placed on a platform shaker and shaken for about 5 days at 25° C.

The cotton-periodic acid slurry is then filtered on a glass Buchner funnel, washed five times with a 3- or 4-liter aliquots of water with intermittent stirring and with filtering after each wash, rinsed four times with 2-liter aliquots of acetone with intermittent stirring and with filtering after each rinse, and subsequently placed on a piece of aluminum foil and dried in air under a hood.

A 0.096 N sodium arsenite solution, standardized by 0.104 M potassium permanganate solution, is prepared and used to titrate aliquots of the periodic acid solution before and after cotton oxidation. From the titer data it is calculated that about 57.8 atoms of oxygen per 100 glucoside units will have been consumed, that is, about 57.8 percent of glucoside rings in the cotton are opened and oxidized to dialdehydes.

The dialdehyde cotton prepared in the foregoing manner gives a strong blue color when added to an aqueous solution comprising 0.4 M sodium carbonate (5 milliliters) and diluted (3:1) Folin Reagent (1 milliliter), thereby giving a positive test for the presence of reducing, i.e., aldehyde, groups. The dialdehyde cottom may be used as a carrier matrix in the method of the invention.

PREPARATION 2

Activation of a Polysaccharide

A proportion (10 grams) of substituted Sephadex G-25 (Pharmacia, supra) is charged together with 50 ml. of water into a 2-necked flask. The product Sephadex G-25 (superfine) is dextran cross-linked with glycerine ether bridges. It is substituted with p-nitrophenoxy-hydroxy-propyl-ether groups to a substitution degree of 200 umol nitro groups per gram of dry substance by reaction with 2,3-epoxy-1-(4-nitrophenoxy)-propane in alkaline milieu. The charge is heated to 35° C. and agitated while at the same time there is added 25 ml. of 5 N aqueous sodium hydroxide and 6 grams of sodium dithionite for reducing the nitro groups into amino groups. After approximately 30 minutes a further 5 grams of sodium dithionite is added. The reduction process is interrupted after approximately 1 hour whereupon neutralization takes place with diluted hydrochloric acid, the solid substance being removed by filtering and washed with distilled water on a suction filter.

10 grams of the above obtained Sephadex product substituted with p-amino-phenoxy-hydroxy-propyl groups is then introduced into a reaction flask together with 100 ml. of a 10 percent solution of thiophosgene in carbon tetrachloride. The flask is sealed with a plug and the mixture agitated for approximately 2 hours. The obtained mixture is cooled in an ice bath whereupon the flask is opened and the contents filtered. The residue of filtration is washed with a 0.1 mol aqueous solution of sodium hydrogen carbonate, distilled water and acetone. The residue is then dried in a drying oven at 60°–80° C. The Sephadex product, obtained according to the above, substituted with p-isothiocyanato-phenoxy-hydroxypropyl groups is swollen in 30 ml. of a 0.1 M aqueous solution of sodium hydrogen carbonate to obtain a matrix carrier which may be used to immobilize restriction endonucleases.

PREPARATION 3

Activation of Agarose

An appropriate vessel is charged with 100 ml. of distilled water and then 100 gms. of agarose beads (Sepharose 4-B, Pharmacia, supra.) is suspended in the water. To the suspension there is added with stirring 100 mg. of finely divided, solid cyanogen bromide. The pH of the resulting mixture is adjusted to 11 by addition of 8 N sodium hydroxide, with vigorous stirring. The pH is monitored continuously thereafter. The adjusted reaction mixture is maintained at a temperature of 20° C. for about 10 minutes and then 200 ml. of cold 1 M phosphate (K+) buffer (pH 7.2) is added with continued stirring. The resulting suspension is then filtered and the residue washed on a sintered glass funnel with 20–30 volumes of the cold buffer. The washed residue is CNBr-activated agarose, which may be stored at 4° C. in an equal volume of buffer, for use within 48–72 hours.

PREPARATION 4

Glass Matrix

Porous glass beads (Potter Industries, Inc., Hasbrouck Heights, N.J.) are cleaned by soaking in 1.2 M hydrochloric acid for 30 minutes. The beads are then transferred to a furnace and the temperature raised slowly to 550° C., and maintained at that temperature for 3 hours. After cooling, the glass is immersed in and equilibrated against 0.1 M acetate buffer, pH 5.0 overnight.

PREPARATION 5

A solution of 100 $\mu$g/ml Lambda phage DNA is prepared in 20 mM of tris(hydroxymethyl) aminomethane, 7 mM magnesium chloride, 2 mM 2-mercaptoethanol and 100 $\mu$g/ml autoclaved gelatin.

PREPARATION 6

A solution of 100 $\mu$g/ml of SV 40 DNA is prepared in 100 mM of tris(hydroxymethyl) aminomethane, 5 mM magnesium chloride and 100 $\mu$g/ml of autoclaved gelatin.

PREPARATION 7

A solution of 100 $\mu$g/ml of adenovirus type 2 DNA is prepared in 100 mM of tris(hydroxymethyl) aminomethane, 5 mM magnesium chloride and 100 $\mu$g/ml. of autoclaved gelatin.

EXAMPLE 1

A portion of the fibrous dialdehyde cotton (about 2.5 grams) prepared according to the method of Preparation 1, supra, is packed in a stainless steel nipple (0.75 inch I.D. by 1.5 inches long). Foamed polyethylene discs are placed at each end of the packed nipple to retain the fibers and the nipple is closed at both ends with stainless steel caps provided with 1/16-inch inlet and outlet fittings, respectively.

A solution is prepared consisting of 4000 units of the restriction endonuclease Bam HI (Endo R·Bam HI, Bethesda Research Laboratories Inc., supra) in 20 m M TRIS-HcL [tris(hydroxymethyl) aminomethane hydrochloride] (pH 7.5), 7 m M magnesium chloride, 2 m M 2-mercaptoethanol and 100 mg/ml of autoclaved gelatin. The endonuclease solution is recirculated through the prepared dialdehyde cotton reactor bed at a rate of 13 ml/minute for about 6 hours. During recirculation, the temperature of the reactor bed is circa. 26° C. At the end of this period, the recirculation is terminated and the reactor bed is washed with a buffer solution of 20 m M potassium phosphate (pH 7.5), 0.5 m M edetic acid, 1 m M dithiothreitol, and 50 percent glycerol pumped through at 13 ml/minute for 15 minutes to obtain a column packing of Bam HI restriction endonuclease bound to dialdehyde cotton.

EXAMPLE 2

To 20 parts of the matrix prepared in Preparation 2, supra, there is added with stirring 2000 units of the restriction endonuclease Eco RI (Endo R·Eco RI, Bethesda Research Laboratories Inc., supra) in 100 m M tris (hydroxymethyl) aminomethane Hcl (pH 7.2), 5 m M magnesium chloride and 100 $\mu$g/ml of autoclaved gelatin at room temperature. The mixture is stirred for about 5 minutes and then allowed to stand for about 15 minutes. The resulting mixture is placed on a vacuum filter and washed with a buffer solution of 10 m M potassium phosphate (pH 7.5), 200 m M sodium chloride, 0.15 percent of a water-soluble phenol derivative of polyethylene glycol, M.W. circa 100 (Triton X-100, Rhom and Haas Company), 1 m M dithiothreitol and 1 m M disodium edetate. The washed product is a compound within the formula (I) above, wherein Eco RI is covalently bonded to an activated polysaccharide.

EXAMPLE 3

10 Grams of the glass beads prepared in Preparation 4, supra, are placed in an appropriate vessel and the vessel is immersed in a 26° C. water bath. To the beads there is added with gentle stirring 2000 units of the restriction endonuclease Eco RI (Endo R·Eco RI, Bethesda Research Laboratories Inc., supra) in 100 m M tris (hydroxymethyl) aminomethane (pH 7.2), 5 mM magnesium chloride and 100 μg/ml of autoclaved gelatin at room temperature. The mixture is stirred for about 5 minutes and then allowed to stand for about 15 minutes. The resulting mixture is placed on a vacuum filter and washed with a buffer solution of 10 mM potassium phosphate (pH 7.5), 200 mM sodium chloride, 0.15 percent of a water-soluble phenol derivative of polyethylene glycol, M.W. circa 100 (Triton X-100, Rhom and Haas Company), 1 mM dithiothreitol and 1 mM disodium edetate. The product is a compound within the formula (I) above, wherein the restriction endonuclease Eco RI is chemically bound to glass.

EXAMPLE 4

About 250 parts of freeze-dried cyanogen bromide activated agarose beads (CNBr-activated Sepharose 4B, Pharmacia Fine Chemicals Incorporated, Piscataway, N.J.) are washed and reswollen on a sintered glass filter with 1 mM hydrochloric acid and then washed with distilled water. An appropriate vessel is then charged with 100 parts of the washed gel so obtained. To the gel there is added with stirring, 2000 units of the restriction endonuclease Eco RI (Endo R·Eco RI, Bethesda Research Laboratories Inc., supra) in a coupling mixture of 10 mM phosphate (K+) (pH 7.2), 0.5 mM edetic acid and 50 percent glycerol at room temperature. The mixture is stirred for about 5 minutes and then allowed to stand for about 15 minutes. The resulting mixture is placed on a vacuum filter and washed with a buffer solution of 10 mM potassium phosphate (pH 7.5), 200 mM sodium chloride, 0.15 percent of a water-soluble phenol derivative of polyethylene glycol, M.W. circa 100 (Triton X-100, Rhom and Haas Co., Phil., Pa.), 1 mM dithiothreitol and 1 mM disodium edetate. The product is a compound within the formula (I), supra, wherein the restriction endonuclease EcoRI is covalently bound to the CNBr-activated Sepharose 4B.

Similarly, repeating the general procedure set forth in Example 4, but replacing the restriction endonuclease Eco RI as used therein with a variety of other restriction endonucleases and employing as the coupling mixture a mixture of 10 mM phosphate (K+) (ph 7.2), 0.5 mM edetic acid and 50 percent glycerol and washing the coupled or immobilized enzyme materials with a buffer solution of 0.5 M sodium chloride, 25 mM of TRIS (hydroxymethyl) aminomethane hydrochloride (pH 7.5), 10 percent glycerol and 1 mM of dithiothreitol, compounds of the formula (I) above are obtained which are biochemically active in the recognition and cleavage of specific palindromes out of DNA. The restriction endonucleases employed, the solvent mixtures employed in their use (digestion solvent) and the storage solutions for storing them used are shown in Table 1, below.

TABLE I

| Restriction Endonuclease | Digestion Solvent | Storage Solution |
|---|---|---|
| Alu I | 6mM Tris HCl (pH 7.5)* | 0.05M phosphate (K+) (pH 7.3) |
| | 6mM MgCl$_2$ | 2mM 2-mercaptoethanol |
| | 6mM 2-mercaptoethanol | 1.0mM Na$_2$ EDTA** |
| | 100 μg/ml autoclaved gelatin | |
| | 50mM sodium chloride | 50% glycerol stored at −20° C. |
| Bam HI | 20mM Tris HCl (pH 7.4)* | 0.05M phosphate (K+) (pH 7.4) |
| | 7mM MgCl$_2$ | 0.5mM dithiothreitol |
| | 7mM 2-mercaptoethanol | 1mM Na$_2$ EDTA** |
| | 100 μg/ml autoclaved gelatin | 50% glycerol stored at −20° C. |
| Pst I | 20mM Tris HCl (pH 7.5)* | 0.05M KCl 0.15% Triton X-100 |
| | 10mM MgCl$_2$ | 0.01M Tris HCl (pH 7.4)* |
| | 50mM (NH$_4$)$_2$SO$_4$ | 0.1mM Na$_2$ EDTA |
| | 100 μg/ml autoclaved gelatin | 1mM dithiothreitol |
| | | 50% glycerol |
| Hae II | 6mM Tris HCl (pH 7.5)* | 0.01M Tris-HCl (pH 7.4)* |
| | 6mM MgCl$_2$ | 0.1mM Na$_2$ EDTA** |
| | 1mM dithiothreitol | 1mM dithiothreitol |
| | 100 μg/ml autoclaved gelatin | 0.05M KCl |
| | | 50% glycerol Enzyme is stored at −20° C. |
| Hae III | 50mM Tris HCl (pH 7.5)* | 0.05M KCl |
| | 5mM MgCl$_2$ | 0.01M Tris HCl (pH 7.4)* |
| | 1mM dithiothreitol | 0.1mM dithiothreitol |
| | 100 μg/ml autoclaved gelatin | 50% glycerol |
| Hind III | 20mM Tris HCl (pH 7.4)* | 0.2M NaCl |
| | 7mM MgCl$_2$ | 10mM Tris HCl (pH 7.4)* |
| | 60mM NaCl | 0.5mM Na$_2$ EDTA** |
| | 100 μg/ml autoclaved gelatin | 1mM dithiothreitol |
| | | 50% glycerol |
| Hpa I | 20mM Tris HCl (pH 7.4)* | 20mM Tris HCl (pH 7.5)* |
| | 10mM MgCl$_2$ | 0.5mM Na$_2$ EDTA** |
| | 1mM dithiothreitol | 1mM dithiothreitol |
| | 6mM KCl | 50% glycerol |
| | 100 μg/ml autoclaved gelatin | |
| Hpa II | 20mM Tris HCl (pH 7.4)* | 20mM Tris HCl (pH 7.5)* |
| | 7mM MgCl$_2$ | 5mM Na$_2$ EDTA** |
| | 1mM dithiothreitol | 1mM dithiothreitol |
| | 100 μg/ml autoclaved gelatin | 50% glycerol |
| Taq I | 20mM Tris HCl (pH 7.5)* | 0.05M KCl |
| | 10mM MgCl$_2$ | 0.01M Tris HCl (pH 7.4)* |
| | 50mM (NH$_4$)$_2$SO$_4$ | 0.1mM Na$_2$ EDTA** |
| | 100 μg/ml autoclaved gelatin | 1mM dithiothreitol |
| Hha I | 50mM Tris HCl (pH 7.4)* | 50mM phosphate (K+) (pH 7.4) |
| | 5mM MgCl$_2$ | 1mM dithiothreitol |
| | 0.5mM dithiothreitol | 50mM NaCl |
| | 100 μg/ml autoclaved gelatin | 50% glycerol |

*Tris (hydroxymethyl) aminomethane hydrochloride
**disodium edetate

EXAMPLE 5

An appropriate vessel is charged with 5 grams of washed (with distilled water) chitin (moist particles, 10 to 50 mesh, containing circa 50% by weight of water). To the charge there is added with stirring at room temperature (circa 26° C.), 20 units of the restriction endonuclease Alu I (Endo R·Alu I, Bethesda Research Laboratories Inc., supra) in a mixture of 6 mM tris (hydroxymethyl) aminomethane hydrochloride, 6 mM magnesium chloride, 6 mM 2-mercaptoethanol, 50 mM sodium chloride and 100 ug/ml autoclaved gelatin. After about 15 minutes an aqueous glutaraldehyde solution is added with continued stirring until the resulting reaction mixture has a 2 percent concentration of glutaraldehyde. The resulting reaction mixture is allowed to stand for 30 minutes at 26° C. and then for 8 hours at 5° C. At the end of that period the mixture is filtered on a sintered glass funnel and the solid residue washed with buffer solution (50 m M potassium phosphate, pH 7.3, 1 m M disodium edetate, 2 m M 2-mercaptoethanol and 50 percent glycerol). The washed solids are chitin particles cross-linked by the glutaraldehyde to the restriction endonuclease. The bonding of the endonuclease can be between the amino, hydroxyl or sulfhydryl groups of the endonuclease and the hydroxyl and amino groups of the modified chitin and the aldehyde group of the glutaraldehyde.

The following Examples show the use of the compositions of the invention.

EXAMPLE 6

A portion of the solution of Lambda phage DNA prepared in Preparation 5, supra, is recirculated through the reactor bed of Example 1, supra, at a rate of 13 ml/minute for about 15 minutes and then held. The reactor bed is heated to a temperature of circa 37° C. for a period of about 15 minutes and then the incubated solution removed and allowed to cool at room temperature. The cooled solution is then fractionated on an agarose slab gel by electrophoresis using the Method of Studies, J. Mol. Biology, 79, 237 (1973) at 175 volts, 50 ma for 1.25 hours at room temperature. When the slab is viewed under ultra-violet radiation it may be seen that the DNA was cleaved at 5'-G↓GATCC-3' (based on the cleaving pattern using a control enzyme).

EXAMPLE 7

To 10 parts of the compound prepared in Example 2, supra, there is added 100 parts of the Preparation 5, supra. The resulting reaction mixture is incubated for 1 hour at 37° C. and then allowed to cool at room temperature. The cooled mixture is filtered to remove solids and the filtrate is loaded on an agarose slab gel for fractionation by electrophoresis (Method of Studies, supra). When the slab is observed, it is seen that the DNA has been cleaved at 5'G↓AATTC-3' (based on the cleaving pattern using a control enzyme).

Similarly, repeating the above procedure but replacing the preparation of Example 2 as used therein with 5 grams of the glass beads prepared in Example 3, supra, the same DNA sequence is cleaved.

Again repeating the above procedure but replacing the preparation of Example 2 as used therein with the compound prepared in Examples 4–5, supra, it is seen that the biochemical activity of the parent restriction endonuclease has been retained in the compound of the invention.

EXAMPLE 8

An appropriate vessel is charged with 200 units* of Bam HI in 0.5 ml. of buffer containing 10 mM phosphate (K+), pH 7.2, 0.5 mM of disodium edetate and 50 percent glycerol with 0.5 ml. of packed CNBr-activated agarose from Preparation 3, supra. The resulting slurry is adjusted to 0.15 M phosphate (K+) (pH 7.5), then gently mixed "end over end" at 4° C. for 16 hrs. Residual reactive groups in the agarose are blocked by suspension of the gel slurry in 0.1 M TRIS-HCl (pH 7.5) for 2 hrs. at 4° C. The excess uncoupled endonuclease is removed from the gel by centrifugation, resuspension of the gel in 0.5 N NaCl, 25 mM TRIS-HCl (pH 7.5), 10 percent glycerol, and 1 mM dithiothreitol, followed by recentrifugation. This washing procedure is repeated four more times. Finally, the enzyme coupled gel is equilibrated with 50 mM TRIS-HCl (pH 7.5), 20 percent glycerol, and 1 mM dithiothreitol by washing five times in this buffer. The final gel slurry is stored at 4° C. No Bam HI enzyme could be detected in any of the supernatants derived from washings, indicating quantitative binding of the starting Bam HI. The washed product is a compound within the formula (I) above and upon assay is found to have a specific activity of 3000 units per gram (specific activity is defined as units per gram of enzyme-coupled agarose). Assay for endonuclease activity is carried out in a reaction mixture (40 μl) containing 0.4 to 2 μg Lambda phage, adenovirus type 2 or SV40 DNA, 50 mM NaCl, and 100 μg/ml autoclaved gelatin. The assay mixtures are incubated for 1 hr at 37° C., then centrifuged and the supernatants removed. To these supernatants there is added one-fourth volume of a solution containing 50 percent glycerol and 0.02 percent bromophenol blue.

*A unit of enzyme activity is defined herein as that amount of enzyme required to completely digest 1 μg of Lambda DNA at 37° C. in 60 min. Routinely, enzymatic activity is measured by serial dilution of the enzyme into the linear range to obtain the minimum amount of enzyme necessary to obtain complete digestion.

Adenovirus type 2 or Lambda phage DNA fragments are separated on a 1.4 percent agarose slab gel (10 cm×12 cm) at 100 volts for 3 hrs following procedures previously described (Sharp, et al. (1973) Biochemistry 12, 3055–3063; Sugden, et al. (1975) Anal. Biochem. 68, 36–46). SV40 DNA digests are fractionated on a 1.2 percent agarose slab gel at 200 volts for 2 hrs. using TRIS-borate EDTA buffer (90 mM Tris-borate, pH 8.3, 2.5 mM disodium edetate). The gels are stained with ethidium bromide (1 μg/ml) for 10 min and photograhed during illumination with a shortwave ultraviolet light. The matrix-bound enzyme, lyophilized to dryness from solutions containing 1 percent (w/v) dextran T70, retained greater than 90 percent of its enzymatic activity. Such lyophilized materials may be stored at room temperature without substantial loss of activity, for at least one week.

EXAMPLE 9

Similarly, repeating the procedure of Example 8 supra., but replacing the Bam HI as used therein with an equivalent number of units of Eco RI, a compound of the formula (I) above, wherein the Eco RI is bound to CNBr-activated agarose, is obtained. The compound upon assay shows a specific activity of 11,000 units/gram. The compounds thus prepared are, stable for at least six months and can be reused at least five times without any significant loss of enzymatic activity.

EXAMPLE 10

This example demonstrates that coupling of restriction endonucleases to water-insoluble matrices does not alter their enzymatic properties. A set of six reaction vessels are provided. In two each of the six vessels there is charged on equal proportion of deoxyribonucleic acid of Preparation 5, supra. To another two, the Preparation 6, supra, is charged. To the last two vessels, equal proportions of the Preparation 7, supra. to obtain 2 series of vessels, each series consisting of 3 vessels, each containing a different deoxyribonucleic acid. To each vessel in one series there is then added 200 units of one of the enzyme bound compounds prepared in Example 8, supra. To the remaining vessels in the second series there is added 200 units of unbound Bam HI. The vessels were incubated at 37° for 1 hour and then centrifuged and the supernatants removed. To these supernatants or to reaction mixtures containing unbound enzyme there was added one-fourth volume of a solution containing 50 percent glycerol and 0.02 percent bromophenol blue. The digested DNA was then fractionated as follows. Adenovirus type 2 and Lambda phage DNA fragments were separated on a 1.4 percent agarose slab gel (10 cm×12 cm) at 100 volts for 3 hrs following procedures previously described. SV40 DNA digests were fractionated on a 1.2 percent agarose slab gel at 200 volts for 2 hrs using TRIS-borate EDTA buffer (90 mM Tris-borate, pH 8.3, 2.5 mM disodium edetate. The gels were stained with ethidium bromide (1 µg/ml) for 10 min and photographed during illumination with a shortwave ultraviolet light.

The above procedure was then repeated, except that the bound enzyme Bam HI of Example 8 was replaced with an equal proportion of the bound Eco RI of Example 9, supra. and the unbound Bam HI was replaced with an equal proportion of unbound Eco RI.

The fragmentation pattern of Lambda phage, adenovirus type 2 or SV40 DNA produced by incubation with the immobilized enzymes was identical to that produced with free enzymes. Phage Lambda DNA digestion with Bam HI or Eco RI produced the expected pattern of six fragments. Adenovirus type 2 DNA was converted to four fragments by Bam HI and six fragments by Eco RI. Both enzymes converted SV40 DNA from superhelical component I to linear component III. In all cases, when bound endonuclease replaced free endonuclease in the reaction, no difference in the patterns of DNA fragments could be detected. These results indicate that both linear and superhelical deoxyribonucleic acids could be effectively digested by the compounds of the invention. In addition, when appropriate incubation conditions were imposed on the Eco RI-coupled agarose, the Eco RI pattern also was obtained. Thus, coupling via the cyanogen bromide linkage apparently does not interfere with critical elements of the active site of the restriction endonucleases. This is particularly important since stereochemical hinderances upon coupling of other enzymes are well documented in other systems; see for example Bar-Eli, et al. (1963) J. Biol. Chem. 238, 1690–1698 and Hornby, et al (1966) Biochem. J. 98, 420–425.

EXAMPLE 11

Representative proportions of the immobilized Bam HI prepared in Example 8, supra, were heated to various temperatures for varying periods of time. Similarly, representative proportions of the immobilized Eco RI prepared in Example 9, supra, were heated to various temperatures for varying periods of time. At the end of the heating period, the products were measured for enzymatic activity as previously described. For control purposes, unbound corresponding enzyme was similarly heat treated and assayed for enzymatic activity. The times and temperatures used and the observed losses of enzyme activity are shown in Table 2, below.

TABLE 2

| Enzyme | Treatment | Loss of Activity (%) |
|---|---|---|
| Example 8 (Bam HI) | None | None |
| | 60° C. - 2 Minutes | 0–10% |
| | 65° C. - 5 Minutes | 10–20% |
| Unbound Bam HI (Control) | None | None |
| | 55° C. - 5 Minutes | 80–90% |
| | 60° C. - 2 Minutes | 100% |
| Example 9 (Eco RI) | None | None |
| | 40° C. - 5 Minutes | None |
| | 45° C. - 5 Minutes | 10% |
| | 50° C. - 5 Minutes | 20% |
| Unbound (Eco RI) (Control) | None | None |
| | 40° C. - 5 Minutes | 100% |

The Table 2 shows that the method of the invention enhanced thermal stability by at least 10° C. for each enzyme. Exposure of stock solutions of the immobilized Bam HI to 65° C. heat for 5 min. resulted in little loss of activity, while the control form treated for 5 min. at 55° C. lost nearly all activity. In fact, treatment of Bam HI at 60° C. for only 2 min. caused complete inactivation, whereas the activity of immobilized Bam HI, according to the method of the invention, remained stable to incubation at 60° C. for 2 min. Free Eco RI, when incubated at 40° C. lost all activity, whereas Eco RI bound to agarose lost only 20 percent of its activity when heat treated at 50° C. The results clearly demonstrate an improved thermal stability upon insolubilization, according to the method of the invention. This is clearly an unexpected advantage making the compounds of formula (I) described above particularly useful for study of deoxyribonucleic acids at high temperatures.

The restriction endonucleases bind tightly to the matrices described herein, and resist washing off even in high salt concentration solutions.

Those skilled in the art will appreciate that many modifications to the preferred embodiments described above may be made without departing from the spirit and the scope of the invention. For example two or more restriction endonucleases may be immobilized on a single water-insoluble matrix to provide a compound of the formula (I) above, wherein R is the residue of different restriction endonucleases. Such compounds are useful to digest deoxyribonucleic acids according to the plurality of endonuclease activities. Similarly, one may immobilize a restriction endonuclease on a water-insoluble matrix to which there is previously or subsequently bound a dissimilar enzyme, for example alkaline phosphatase. Such a compound would be useful, for example, as taught by U.S. Pat. No. 4,039,382.

What is claimed:

1. A biochemically active, immobilized, restriction endonuclease comprising restriction endonuclease Bam HI chemically bonded to cyanogen bromide activated agarose.

2. A biochemically active, immobilized, restriction endonuclease comprising restriction endonuclease Eco RI chemically bonded to cyanogen bromide activated agarose.

* * * * *